United States Patent
Song et al.

(10) Patent No.: US 12,338,288 B2
(45) Date of Patent: Jun. 24, 2025

(54) INTERLEUKIN-4 RECEPTOR ANTIBODY AND APPLICATION THEREOF

(71) Applicant: Shandong Boan Biotechnology Co., Ltd., Shandong (CN)

(72) Inventors: Deyong Song, Shandong (CN); Chuangchuang Dong, Shandong (CN); Jing Han, Shandong (CN)

(73) Assignee: Shandong Boan Biotechnology Co., Ltd., Yantai (CN)

( * ) Notice: Subject to any disclaimer, the term of this patent is extended or adjusted under 35 U.S.C. 154(b) by 932 days.

(21) Appl. No.: 17/601,837

(22) PCT Filed: Jun. 23, 2020

(86) PCT No.: PCT/CN2020/097686
§ 371 (c)(1),
(2) Date: Oct. 6, 2021

(87) PCT Pub. No.: WO2020/239134
PCT Pub. Date: Dec. 3, 2020

(65) Prior Publication Data
US 2022/0162328 A1    May 26, 2022

(30) Foreign Application Priority Data

May 29, 2019    (CN) .................. 201910456273.X
May 29, 2019    (CN) .................. 201910456605.4

(51) Int. Cl.
| | |
|---|---|
| C07K 16/28 | (2006.01) |
| A61K 45/06 | (2006.01) |
| A61P 11/06 | (2006.01) |
| A61K 38/20 | (2006.01) |
| A61K 39/00 | (2006.01) |

(52) U.S. Cl.
CPC .......... C07K 16/2866 (2013.01); A61K 45/06 (2013.01); A61P 11/06 (2018.01); A61K 38/20 (2013.01); A61K 2039/505 (2013.01)

(58) Field of Classification Search
CPC ............ C07K 16/2866; C07K 2317/21; C07K 2317/33; C07K 2317/52; C07K 2317/73; C07K 2317/76; C07K 2317/92; C07K 2319/00; C07K 2317/565; A61K 45/06; A61K 38/20; A61K 2039/505; A61P 11/06; A61P 29/00; A61P 37/08; A61P 37/02
See application file for complete search history.

(56) References Cited

U.S. PATENT DOCUMENTS

| | | |
|---|---|---|
| 2004/0043921 A1 | 3/2004 | Bonnefoy et al. |
| 2008/0160035 A1 | 7/2008 | Stevens et al. |

FOREIGN PATENT DOCUMENTS

| | | |
|---|---|---|
| CN | 102197052 | 9/2011 |
| CN | 104755495 | 7/2015 |
| CN | 104995212 | 10/2015 |
| CN | 105753987 | 7/2016 |
| CN | 106604744 | 4/2017 |
| CN | 107474134 | 12/2017 |
| CN | 108373505 | 8/2018 |
| IN | 2008CHENP2006 | 6/2007 |
| JP | 2015-534548 | 12/2015 |
| RU | 2015109716 | 10/2016 |
| WO | WO 2017/211319 | 12/2017 |
| WO | WO2020239134 | 12/2020 |

OTHER PUBLICATIONS

International Preliminary Report on Patentability in International Appln. No. PCT/CN2020/097686, dated Sep. 23, 2020, 12 pages (with English Translation).
International Search Report and Written Opinion in International Appln. No. PCT/CN2020/097686, dated Sep. 23, 2020, 22 pages (with English Translation).
LaPorte et al., "Molecular and Structural Basis of Cytokine Receptor Pleiotropy in the Interleukin-4/13 System," Cell, Jan. 2008, 132(2):259-272.

*Primary Examiner* — Chun W Dahle
*Assistant Examiner* — Grace H Lunde
(74) *Attorney, Agent, or Firm* — Fish & Richardson P.C.

(57) ABSTRACT

Provided are an antibody or an antigen binding fragment thereof which specifically binds to the IL-4R antigen, and a preparation method, a composition and an application. The IL-4R antibody may be used for preparing a drug which treats and/or prevents inflammation or allergies, or for immunological IL-4R antigen detection.

9 Claims, 5 Drawing Sheets
Specification includes a Sequence Listing.

```
                        SEQUENCE LISTING

<160> NUMBER OF SEQ ID NOS: 28

<210> SEQ ID NO 1
<211> LENGTH: 107
<212> TYPE: PRT
<213> ORGANISM: Artificial Sequence
<220> FEATURE:
<223> OTHER INFORMATION: The sequence is artificially synthesized

<400> SEQUENCE: 1

Glu Ile Val Met Thr Gln Ser Pro Ser Ser Leu Ser Ala Ser Leu Gly
1               5                   10                  15

Asp Arg Val Thr Ile Thr Cys Arg Ala Ser Gln Asn Ile Gly Ser Arg
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Trp
                85                  90                  95

Thr Phe Gly Gln Gly Thr Lys Leu Glu Ile Lys
            100                 105

<210> SEQ ID NO 2
<211> LENGTH: 119
<212> TYPE: PRT
<213> ORGANISM: Artificial Sequence
<220> FEATURE:
<223> OTHER INFORMATION: The sequence is artificially synthesized

<400> SEQUENCE: 2

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Thr Thr Val Arg Gly Val Leu Tyr Trp Gly Gln Gly
            100                 105                 110

Thr Leu Val Thr Val Ser Ser
        115

<210> SEQ ID NO 3
<211> LENGTH: 6
<212> TYPE: PRT
<213> ORGANISM: Artificial Sequence
<220> FEATURE:
<223> OTHER INFORMATION: The sequence is artificially synthesized
```

-continued

```
<400> SEQUENCE: 3

Gln Asn Ile Gly Ser Arg
1               5

<210> SEQ ID NO 4
<211> LENGTH: 3
<212> TYPE: PRT
<213> ORGANISM: Artificial Sequence
<220> FEATURE:
<223> OTHER INFORMATION: The sequence is artificially synthesized

<400> SEQUENCE: 4

Lys Ala Ser
1

<210> SEQ ID NO 5
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 5

Gln Gln Tyr Asn Ser Tyr Ser Trp Thr
1               5

<210> SEQ ID NO 6
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 6

Gly Phe Thr Phe Ser Ser Tyr Ala
1               5

<210> SEQ ID NO 7
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 7

Ile Ser Tyr Asp Gly Ser Asn Lys
1               5

<210> SEQ ID NO 8
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 8

Ala Arg Gly Leu Thr Thr Val Arg Gly Val Leu Tyr
1               5                   10

<210> SEQ ID NO 9
<211> LENGTH: 107
<212> TYPE: PRT
<213> ORGANISM: Artificial Sequence
<220> FEATURE:
<223> OTHER INFORMATION: The sequence is artificially synthesized
```

<400> SEQUENCE: 9

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Arg
            20                  25                  30

Leu Ala Trp Tyr Gln Gln Lys Pro Gly Lys Ala Pro Lys Leu Leu Val
        35                  40                  45

Tyr Trp Ala Ser Ser Leu Glu Ser Gly Val Pro Ser Arg Phe Ser Gly
    50                  55                  60

Ser Gly Ser Gly Thr Glu Phe Thr Leu Ala Ile Ser Ser Leu Gln Pro
65                  70                  75                  80

Asp Asp Phe Gly Thr Tyr Tyr Cys Gln Gln Tyr Thr Ser Tyr Ser Trp
            85                  90                  95

Thr Phe Gly Gln Gly Thr Lys Leu Glu Ile Lys
            100                 105

<210> SEQ ID NO 10
<211> LENGTH: 119
<212> TYPE: PRT
<213> ORGANISM: Artificial Sequence
<220> FEATURE:
<223> OTHER INFORMATION: The sequence is artificially synthesized

<400> SEQUENCE: 10

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Leu Thr Thr Val Arg Gly Val Leu Tyr Trp Gly Gln Gly
            100                 105                 110

Thr Leu Val Thr Val Ser Ser
        115

<210> SEQ ID NO 11
<211> LENGTH: 6
<212> TYPE: PRT
<213> ORGANISM: Artificial Sequence
<220> FEATURE:
<223> OTHER INFORMATION: The sequence is artificially synthesized

<400> SEQUENCE: 11

Gln Ser Ile Ser Thr Arg
1               5

<210> SEQ ID NO 12
<211> LENGTH: 3
<212> TYPE: PRT
<213> ORGANISM: Artificial Sequence
<220> FEATURE:
<223> OTHER INFORMATION: The sequence is artificially synthesized

<400> SEQUENCE: 12

Trp Ala Ser
1

<210> SEQ ID NO 13
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 13

Gln Gln Tyr Thr Ser Tyr Ser Trp Thr
1               5

<210> SEQ ID NO 14
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 14

Gly Phe Thr Phe Ser Ser Tyr Ala
1               5

<210> SEQ ID NO 15
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 15

Ile Ser Tyr Asp Gly Ser Asn Lys
1               5

<210> SEQ ID NO 16
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 16

Ala Arg Gly Leu Thr Thr Val Arg Gly Val Leu Tyr
1               5                   10

<210> SEQ ID NO 17
<211> LENGTH: 106
<212> TYPE: PRT
<213> ORGANISM: Artificial Sequence
<220> FEATURE:
<223> OTHER INFORMATION: The sequence is artificially synthesized

<400> SEQUENCE: 17

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Arg Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro

```
                65                  70                  75                  80
Asp Asp Phe Ala Thr Tyr Tyr Cys Gln Gln Tyr Asn Arg Tyr Phe Thr
                    85                  90                  95

Phe Gly Gln Gly Thr Lys Leu Glu Ile Lys
                100                 105

<210> SEQ ID NO 18
<211> LENGTH: 117
<212> TYPE: PRT
<213> ORGANISM: Artificial Sequence
<220> FEATURE:
<223> OTHER INFORMATION: The sequence is artificially synthesized

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Ile His Trp Val Arg Gln Ala Pro Gly Lys Gly Leu Glu Trp Val
            35                  40                  45

Ala Val Ile Ser Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Tyr Tyr Tyr Gly Met Asp Val Trp Gly Gln Gly Thr Thr
                100                 105                 110

Val Thr Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: The sequence is artificially synthesized

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Phe Asn Ser Trp
                20                  25                  30

Leu Ala Trp Tyr Gln Gln Lys Pro Gly Lys Ala Pro Lys Leu Leu Ile
            35                  40                  45

Tyr Lys Ser Ser Arg Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Gly Tyr Ser Trp
                85                  90                  95

Thr Phe Gly Gln Gly Thr Lys Val Glu Ile Lys
                100                 105

<210> SEQ ID NO 20
<211> LENGTH: 119
<212> TYPE: PRT
<213> ORGANISM: Artificial Sequence
<220> FEATURE:
```

<223> OTHER INFORMATION: The sequence is artificially synthesized

<400> SEQUENCE: 20

Gln Val Gln Leu Val Glu Ser Arg Gly Gly Ala Val Gln Pro Gly Arg
1               5                   10                  15

Ser Leu Arg Val Ser Cys Ala Ala Ser Gly Phe Thr Phe Ser Ser His
            20                  25                  30

Gly Met Asp Trp Val Arg Gln Val Pro Gly Lys Gly Leu Glu Trp Val
        35                  40                  45

Ala Val Ile Ser Tyr Asp Gly Lys Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Val Lys Glu Ser Arg Tyr Tyr Tyr Gly Met Asp Val Trp Gly Gln Gly
            100                 105                 110

Thr Thr Val Thr Val Ser Ser
        115

<210> SEQ ID NO 21
<211> LENGTH: 107
<212> TYPE: PRT
<213> ORGANISM: Artificial Sequence
<220> FEATURE:
<223> OTHER INFORMATION: The sequence is artificially synthesized

<400> SEQUENCE: 21

Asp Ile Val Met Thr Gln Ser Pro Ser Thr Leu Ser Ala Ser Val Gly
1               5                   10                  15

Asp Arg Val Thr Ile Thr Cys Arg Ala Ser Pro Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ser Ser Arg Leu Glu Ser Gly Val Pro Ser Arg Phe Ser Gly
    50                  55                  60

Asn Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Gly Tyr Ser Trp
                85                  90                  95

Thr Phe Gly Gln Gly Thr Lys Val Glu Ile Lys
            100                 105

<210> SEQ ID NO 22
<211> LENGTH: 119
<212> TYPE: PRT
<213> ORGANISM: Artificial Sequence
<220> FEATURE:
<223> OTHER INFORMATION: The sequence is artificially synthesized

<400> SEQUENCE: 22

Gln Val Gln Leu Val Glu Ser Gly Gly Ala Val Gln Pro Gly Arg
1               5                   10                  15

Ser Leu Arg Val Ser Cys Ala Ala Ser Gly Phe Thr Phe Ser Ser His
            20                  25                  30

Gly Met Asp Trp Val Arg Gln Val Pro Gly Lys Gly Leu Glu Trp Val
        35                  40                  45

Ala Val Ile Ser Tyr Asp Gly Lys Lys Lys Tyr Tyr Ala Asp Ser Val

```
                50              55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                     85                  90                  95

Val Lys Glu Ser Arg Tyr Tyr Tyr Gly Met Asp Val Trp Gly Gln Gly
                100                 105                 110

Thr Thr Val Thr Val Ser Ser
            115

<210> SEQ ID NO 23
<211> LENGTH: 107
<212> TYPE: PRT
<213> ORGANISM: Artificial Sequence
<220> FEATURE:
<223> OTHER INFORMATION: The sequence is artificially synthesized

<400> SEQUENCE: 23

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Thr Arg Arg
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Val Ser Phe Ser Arg
                 85                  90                  95

Thr Phe Gly Gln Gly Thr Lys Val Glu Ile Lys
            100                 105

<210> SEQ ID NO 24
<211> LENGTH: 116
<212> TYPE: PRT
<213> ORGANISM: Artificial Sequence
<220> FEATURE:
<223> OTHER INFORMATION: The sequence is artificially synthesized

<400> SEQUENCE: 24

Gln Val Gln Leu Val Glu Ser Gly Gly Gly Val Val Gln Pro Gly Arg
 1               5                  10                  15

Ser Leu Arg Leu Ser Cys Ala Ala Ser Gly Leu Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Phe Gly Tyr Phe Asp Leu Trp Gly Arg Gly Thr Leu Val
            100                 105                 110

Thr Val Ser Ser
            115
```

```
<210> SEQ ID NO 25
<211> LENGTH: 326
<212> TYPE: PRT
<213> ORGANISM: Artificial Sequence
<220> FEATURE:
<223> OTHER INFORMATION: The sequence is artificially synthesized

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 26
<211> LENGTH: 107
<212> TYPE: PRT
<213> ORGANISM: Artificial Sequence
<220> FEATURE:
```

<223> OTHER INFORMATION: The sequence is artificially synthesized

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 219
<212> TYPE: PRT
<213> ORGANISM: Artificial Sequence
<220> FEATURE:
<223> OTHER INFORMATION: The sequence is artificially synthesized

<400> SEQUENCE: 27

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 28

```
<211> LENGTH: 451
<212> TYPE: PRT
<213> ORGANISM: Artificial Sequence
<220> FEATURE:
<223> OTHER INFORMATION: The sequence is artificially synthesized

<400> SEQUENCE: 28

Glu Val Gln Leu Val Glu Ser Gly Gly Gly Leu Glu Gln Pro Gly Gly
 1               5                  10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450
```

INTERLEUKIN-4 RECEPTOR ANTIBODY AND APPLICATION THEREOF

CROSS-REFERENCE TO RELATED APPLICATIONS

This application is a National Stage application under 35 U.S.C. § 371 of International Application No. PCT/CN2020/097686, filed on Jun. 23, 2020, which claims the benefit of Chinese Application No. 201910456605.4, filed May 29, 2019, and Chinese Application No. 201910456273.X, filed May 29, 2019. The disclosures of the prior application are incorporated by reference in their entirety.

SEQUENCE LISTING

The instant application contains a Sequence Listing which has been submitted electronically is ASCII format and is hereby incorporated by reference in its entirety. Said ASCII copy, created on Mar. 3, 2025, is named 48644-0007US1_ST25 and is 25,993 bytes in size.

TECHNICAL FIELD

The present invention relates to the technical field of biomedicine or biological pharmaceutics, and more specifically, to a human anti-IL-4R antibody, and an encoding sequence, a preparation method, a composition and an application thereof.

BACKGROUND ART

Interleukin-4 (IL-4), a cytokine with various biological functions, is produced by activated type-2 helper T (Th2) cells and is a hydrophobic globular protein consisted of 129 amino acid residues. IL-4 has many target cells such as T cells, B cells, hematopoietic cells, fibroblasts and various tumor cells, which all have IL-4 receptors. There are two types of interleukin-4 receptors (IL-4R): type I receptor, which is mainly composed of IL-4Rα chain and γc chain, and is mainly expressed on the surface of hematopoietic cells; and type II receptor, which is composed of IL-4Rα chain and IL-13Rα1 chain, and is mainly expressed on the surface of non-hematopoietic cells and tumor cells (La Porte S L, Juo Z S, Vaclavikova J, et al. Cell, 2008, 132 (2):259-272). IL-4Rα is a key component of type I and type II receptors in the type II inflammatory pathway. Blocking IL-4Rα can simultaneously block two potent regulators IL-4 and IL-13 of type 2 immune response. In the type II inflammatory pathway, Th2 cells (T helper 2, belonging to CD4+T cells) play a key role. Type 2 immunity is a special immune response that comprises innate immunity and adaptive immunity and promotes the formation of an immunologic barrier on the mucosal surface to eliminate pathogens. The type II inflammatory pathway plays an essential role in the development of allergic diseases. Therefore, IL-4Rα is one of the key targets for the targeted treatment of allergic diseases (including atopic dermatitis, asthma, idiopathic urticaria, chronic nasal polyp sinusitis, food allergy, etc.).

Currently, antibody drug dupilumab (Sanofi Co., Ltd.) targeting interleukin 4 receptor (IL-4R) has been approved for marketing by the US FDA under the trade name DUPIXENT®. The antibody is an interleukin 4 receptor (IL-4R) antagonist and can inhibit IL-4 and IL-13 signals. Currently, the antibody injection is used for the treatment of atopic dermatitis and asthma indications.

However, facing the patient need for drugs, especially for antibody drugs for disease treatment, there is still an urgent need for IL-4R antibody drugs with lower immunogenicity, longer half-life, and better drug effects.

SUMMARY OF THE INVENTION

The present invention provides an antibody or an antigen-binding fragment thereof having a new amino acid sequence. The antibody or the antigen-binding fragment thereof includes a monoclonal antibody, a polyclonal antibody, a chimeric antibody, a humanized antibody, and a Fab, Fab', F(ab')2, Fv, scFv or dsFv fragment, etc.

The antibody or the antigen-binding fragment thereof provided by the present invention comprises:
1) 3 light chain complementarity determining regions, wherein LCDR1 amino acid sequence is as shown in SEQ ID NO: 11, LCDR2 amino acid sequence is as shown in SEQ ID NO: 12, and LCDR3 amino acid sequence is as shown in SEQ ID NO: 13, and
3 heavy chain complementarity determining regions, wherein HCDR1 amino acid sequence is as shown in SEQ ID NO: 14, HCDR2 amino acid sequence is as shown in SEQ ID NO: 15, and HCDR3 amino acid sequence is as shown in SEQ ID NO: 16; or
2) 3 light chain complementarity determining regions, wherein LCDR1 amino acid sequence is as shown in SEQ ID NO: 3, LCDR2 amino acid sequence is as shown in SEQ ID NO: 4, and LCDR3 amino acid sequence is as shown in SEQ ID NO: 5, and
3 heavy chain complementarity determining regions, wherein HCDR1 amino acid sequence is as shown in SEQ ID NO: 6, HCDR2 amino acid sequence is as shown in SEQ ID NO: 7, and HCDR3 amino acid sequence is as shown in SEQ ID NO: 8.

In one aspect of the present invention, the light chain of the antibody or the antigen-binding fragment thereof comprises a light chain variable region (VL), and the light chain variable region comprises any amino acid sequence as shown in SEQ ID NO:1 or SEQ ID NO:9, or comprises an amino acid sequence having at least 80%, 85% or 90% sequence identity to the amino acid sequence of the above-mentioned light chain variable region. The heavy chain of the antibody or the antigen-binding fragment thereof comprises a heavy chain variable region (VH), and the heavy chain variable region comprises any amino acid sequence as shown in SEQ ID NO:2 or SEQ ID NO:10, or comprises an amino acid sequence having at least 80%, 85% or 90% sequence identity to the amino acid sequence of the above-mentioned heavy chain variable region. Preferably, the antibody or the antigen-binding fragment thereof comprises the following light and heavy chain variable region sequences, comprising:
1) the light chain variable region of the amino acid sequence as shown in SEQ ID NO:1 and/or the heavy chain variable region comprising the amino acid sequence as shown in SEQ ID NO:2; or
2) the light chain variable region of the amino acid sequence as shown in SEQ ID NO:9 and/or the heavy chain variable region of the amino acid sequence as shown in SEQ ID NO: 10.

In one aspect, the antibody or the antigen-binding fragment thereof comprises a heavy chain constant region, wherein the heavy chain constant region comprises a γ-1, γ-2, γ-3 or γ-4 human heavy chain constant region or the variant of the human heavy chain constant region, and preferably, the sequence of the heavy chain constant region is ASTKGPSVFPLAPCSRSTSESTAALGCLVKDYF-PEPVTVSWNSGALTSGVHT FPAVLQSSGLYS-LSSVVTVPSSSLGTKTYTCNVDHKPSNTKVDKRVES KYGP PCPPCPAPEFLGGPSVFLFPPKPKDTLMISRTPE-VTCVVVDVSQEDPEVQFN WYVDGVEVHNAKTKPREEQFN-STYRVVSVLTVLHQDWLNGKEYKCKVSN KGLPSSIEKTISKAKGQPREPQVYTLPPSQEEMT-KNQVSLTCLVKGFYPSDIA VEWESNGQPEN-NYKTTPPVLDSDGSFFLY-SRLTVDKSRWQEGNVFSCSVMH EALHNHYTQKSLSLSLG (SEQ ID NO: 25). In one aspect, the antibody further comprises a light chain constant region, wherein the light chain constant region comprises a λ or κ human light chain constant region, and preferably the sequence of the light chain constant region is RTVAAPSVFIFPPSDEQLKSGTASVVCLLNNFY-PREAKVQWKVDNALQSGN SQESVTEQDSKDSTYS-LSSTLTLSKADYEKHKVYACEVTHQGLSSPVTKSFN RGEC (SEQ ID NO: 26).

In one aspect of the present invention, the binding antigen of the above-mentioned antibody or the antigen-binding fragment thereof binds to IL-4R antigen, and preferably, the IL-4R is human IL-4R.

The present invention also provides a nucleic acid sequence encoding the antibody or antigen-binding fragment thereof that binds to human IL-4R.

In one aspect of the present invention, the nucleic acid encodes the antibody or the antigen-binding fragment thereof comprising the following amino acid sequences of the light chain and heavy chain complementarity determining regions:
1) LCDR1 amino acid sequence as shown in SEQ ID NO: 11, LCDR2 amino acid sequence as shown in SEQ ID NO: 12, and LCDR3 amino acid sequence as shown in SEQ ID NO: 13, and HCDR1 amino acid sequence as shown in SEQ ID NO: 14, HCDR2 amino acid sequence as shown in SEQ ID NO: 15, and HCDR3 amino acid sequence as shown in SEQ ID NO: 16; or
2) LCDR1 amino acid sequence as shown in SEQ ID NO: 3, LCDR2 amino acid sequence as shown in SEQ ID NO: 4, and LCDR3 amino acid sequence as shown in SEQ ID NO: 5, and HCDR1 amino acid sequence as shown in SEQ ID NO: 6, HCDR2 amino acid sequence as shown in SEQ ID NO: 7, and HCDR3 amino acid sequence as shown in SEQ ID NO: 8;
3) the light chain variable region of the amino acid sequence as shown in SEQ ID NO:1 and/or the heavy chain variable region comprising the amino acid sequence as shown in SEQ ID NO:2; or
4) the light chain variable region of the amino acid sequence as shown in SEQ ID NO:9 and/or the heavy chain variable region of the amino acid sequence as shown in SEQ ID NO: 10.

The present invention relates to nucleic acids that hybridize with the above-mentioned sequences and have at least 50%, preferably at least 70%, and more preferably at least 80% identity between the two sequences. The present invention particularly relates to a nucleic acid that can hybridize to the nucleic acid of the present invention under stringent conditions. In the present invention, "stringent conditions" refer to: (1) hybridization and elution at lower ionic strength and higher temperature, such as 0.2×SSC, 0.1% SDS, and at 60° C.; or (2) adding a denaturing agent during hybridization, such as 50% (v/v) formamide, 0.1% calf serum/0.1% Ficoll, and at 42° C.; or (3) hybridization that only occurs when the identity between the two sequences is at least 90%, and more preferably at least 95%. The polypeptide encoded by the hybridizable nucleic acid has the same biological function and activity to that of the mature polypeptide.

Once the relevant sequences are obtained, a recombinant method can be used to obtain the relevant sequences in large numbers. This is usually done by cloning the relevant sequences into vectors, then transferring the cloning vectors into cells, and then isolating the relevant sequences from the proliferated host cells by conventional methods. The biomolecules (a nucleic acid, a protein, etc.) involved in the present invention include the biomolecules that exist in an isolated form.

At present, the DNA sequence encoding the protein (or the fragment or the derivative thereof) of the present invention can be obtained completely through chemical synthesis. The DNA sequence can then be introduced into various existing DNA molecules (or such as vectors) and cells known in the art. In addition, mutations can also be introduced into the protein sequence of the present invention through chemical synthesis.

The present invention also provides a vector comprising a nucleotide sequence encoding the antibody or the antigen-binding fragment thereof that binds to IL-4R, and preferably, the vector is an expression vector. The vector of the present invention includes, but is not limited to, a viral vector, such as an adenovirus vector, a retrovirus vector, and an adeno-associated virus vector; and a non-viral vector, such as a plasmid and a transposon vector, wherein the plasmid vector is preferably a pCDNA3.4 (Life Technology) vector. These vectors can be used to transform appropriate host cells so that the host cells can express proteins.

The present invention also provides a host cell for expressing the antibody or the antigen-binding fragment thereof that binds to human IL-4R, wherein the host cell contains an expression vector encoding the antibody or the antigen-binding fragment thereof that binds to human IL-4R or a nucleic acid encoding the antibody or the antigen-binding fragment thereof that binds to human IL-4R.

The present invention also provides a cell for expressing the antibody or the antigen-binding fragment thereof that binds to IL-4R, wherein the cell comprises an expression vector encoding the antibody or the antigen-binding fragment thereof that binds to IL-4R or a nucleic acid encoding the antibody or the antigen-binding fragment thereof that binds to IL-4R, and preferably, the cell is a host cell comprising the above-mentioned expression vector. In one aspect of the present invention, the host cell expressing the antibody or the antigen-binding fragment thereof that binds to IL-4R includes but is not limited to a mammalian cell, an insect cell, a plant cell, a fungal cell, and a prokaryotic cell. Representative examples include *Escherichia coli* and *Streptomyces*; a bacterial cell of *Salmonella typhimurium*; a fungal cell such as yeast; an insect cell of *Drosophila* S2 or Sf9; and an animal cell such as CHO, COS7, and 293 cells. Preferably, the host cell provided by the present invention for expressing the antibody or the antigen-binding fragment thereof that binds to IL-4R is HEK293.

Transformation of host cells with recombinant DNA can be carried out by conventional techniques well known to a person skilled in the art. When the host is a prokaryote such as *Escherichia coli*, competent cells that can absorb DNA can be harvested after the exponential growth phase and treated with a $CaCl_2$) method. The steps used are well known in the art. Another method is to use $MgCl_2$. If necessary, transformation can also be carried out by an electroporation method. When the host is a eukaryote, the following DNA transfection methods can be used: a calcium phosphate co-precipitation method, and a conventional mechanical method such as microinjection, electroporation, and liposome packaging.

The obtained transformants can be cultured by conventional methods to express the antibody encoded by the gene of the present invention. Depending on the host cell used, the culture medium used for cultivation can be selected from various conventional culture mediums. The culture is performed under conditions suitable for host cell growth. The selected promoter may be induced using an appropriate method (e.g., temperature changes or chemical induction) when host cells are grown to an appropriate density, and the cells are cultured for an additional period.

Recombinant antibodies in the above-mentioned methods can be expressed inside the cells or on the cell membranes, or secreted outside the cells. If necessary, the physical, chemical, and other characteristics can be used to separate and purify the recombinant proteins by various separation methods. These methods are well known to a person skilled in the art. Examples of these methods include but are not limited to: conventional renaturation treatment, treatment by a protein precipitant (salt precipitation), centrifugation, cell lysis by osmosis, sonication, supercentrifugation, molecular sieve chromatography (gel filtration), adsorption chromatography, ion exchange chromatography, high performance liquid chromatography (HPLC), and any other liquid chromatography, and a combination thereof.

According to another aspect of the present invention, further provided is a composition comprising the above-mentioned antibody or the antigen-binding fragment thereof that binds to human IL-4R, and a pharmaceutically acceptable carrier. The pharmaceutically acceptable carrier includes one or more of the following: a pharmaceutically acceptable solvent, a dispersant, an additive, a plasticizer, and a pharmaceutical excipient. Generally, these substances are non-toxic, inert and pharmaceutically acceptable carrier mediums. The formulated pharmaceutical composition can be administrated in conventional routines including (but not limited to) intratumoral, intraperitoneal, intravenous, or topical administration such as injection administration.

The present invention also relates to a kit, which comprises any of the above-mentioned antibody or the antibody fragment that binds to the IL-4R antigen, and a nucleic acid. In one aspect of the present invention, the kit comprises the antibody or the antigen-binding fragment thereof of any one of the following groups of CDR amino acid sequences:

1) LCDR1 amino acid sequence as shown in SEQ ID NO: 11, LCDR2 amino acid sequence as shown in SEQ ID NO: 12, and LCDR3 amino acid sequence as shown in SEQ ID NO: 13, and HCDR1 amino acid sequence as shown in SEQ ID NO: 14, HCDR2 amino acid sequence as shown in SEQ ID NO: 15, and HCDR3 amino acid sequence as shown in SEQ ID NO: 16; or
2) LCDR1 amino acid sequence as shown in SEQ ID NO: 3, LCDR2 amino acid sequence as shown in SEQ ID NO: 4, and LCDR3 amino acid sequence as shown in SEQ ID NO: 5, and HCDR1 amino acid sequence as shown in SEQ ID NO: 6, HCDR2 amino acid sequence as shown in SEQ ID NO: 7, and HCDR3 amino acid sequence as shown in SEQ ID NO: 8.

In one aspect of the present invention, the kit further comprises a detection reagent, a negative control, and a positive control for detecting the IL-4R antigen-antibody reaction.

In another aspect, the present invention relates to the use of the antibody or the antigen-binding fragment thereof, the nucleic acid, the vector or the cell of any one of the preceding aspects in the preparation of a pharmaceutical composition for treating and/or preventing a disease.

In another aspect, the present invention relates to the use of the antibody or the antigen-binding fragment thereof, and the nucleic acid of any one of the preceding aspects in the preparation of a diagnostic and detection kit.

In another aspect, a method for treating or preventing a disease is provided. The method comprises administering the antibody or the antigen-binding fragment, the nucleic acid, the vector, the cell or the pharmaceutical composition of the present invention to a subject in need thereof.

In another aspect, a method for diagnosing and detecting is provided. The method comprises administering the antibody or antigen-binding fragment, the nucleic acid or the kit of the present invention to a subject or a sample in need thereof.

In another aspect, the use of the antibody or the antigen-binding fragment thereof, the nucleic acid, the vector, the cell or the pharmaceutical composition of any one of the preceding aspects for treating and preventing a disease is provided.

In another aspect, the use of the antibody or the antigen-binding fragment thereof, the nucleic acid, or the kit of any one of the preceding aspects for detecting and diagnosing is provided.

According to another aspect of the present invention, the disease is preferably an IL-4R-related disease, and further preferably, the IL-4R-related condition is an inflammation or allergic disease, including asthma, atopic dermatitis, pruritus, neutropenia, allergic reaction, nasal polyp, eosinophilic esophagitis, skin infection, chronic sinusitis, etc.; Preferably, the inflammation or allergic disease is asthma; Further preferably, the treatment and/or prevention of asthma includes reducing the incidence of asthma exacerbations, improving one or more asthma parameters, improving the dependence of a patient on an inhaled corticosteroid and/or a long-acting β agonist, etc.

Through extensive, in-depth research, and mass screening, the inventors have successfully obtained a class of anti-IL-4R antibodies. The experimental results showed that the IL-4R antibodies obtained in the present invention can effectively block the interaction between IL-4R and the ligand thereof. Surprisingly, it was identified that the obtained candidate antibodies have different epitope binding properties with Dupilumab, and has a low immunogenicity, a long half-life in vivo, and a significant in vivo effect in animal models of diseases such as asthma. The present invention has been accomplished on the basis of the above.

DETAILED DESCRIPTION OF EMBODIMENTS

With reference to the following examples, the present invention can be better understood. However, it should be understood that the following examples are presented for exemplary purpose only, and should not be understood as limiting the scope of protection of the present invention in any way.

Example 1. Production of Anti-IL4R Antibody 1.1 Immunization

Figure 1:
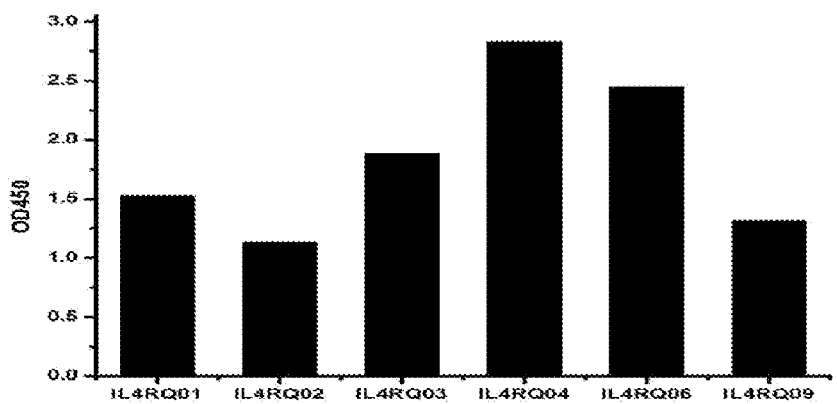
FIG. 1 shows the serum titers of transgenic mice at 5000-fold serum dilution.

After being emulsified with IL4R (Sinobiological, Cat. No. 10402-H08H) and Freund's adjuvant, the fully human antibody transgenic mouse BoAn-hMab from Shandong Boan Co., Ltd. was immunized. Complete Freund's adjuvant was used for the first immunization, and Freund's incomplete adjuvant was used for the secondary immunization and the tertiary immunization. A total of 9 mice were immunized this time. Mice with higher serum titers were selected for booster immunization. After 3 days, the mice were sacrificed and the spleens thereof were taken out for subsequent experiments. The serum titers were mainly detected by ELISA. CBS coating solution (pH 9.6 carbonic acid solution) was used to coat IL4R protein (10402-H08H, Sinobiological Co., Ltd.) at the concentration of 1 g/mL in 100 μL/well at 4° C. overnight; 3% skimmed milk powder was used for blocking at 37° C., 1 h; and the serum was diluted with PBST to 200×, 1000×, 5000×, and 25000×, and was added 100 μL per well. The plate was incubated at 37° C. for 1 h; and then HRP-goat anti-human H+L (474-1006, KPL) was added, and incubated at 37° C. for 1 h. Color development was stopped, after 10 min color development, with 2 M concentrated sulphuric acid and OD450 was measured with a microplate reader. The detected serum titers were as shown FIG. 1.

1.2 Construction of Phage Library

The spleen cells of the immunized mice were taken out and Trizol (Thermo Scientific, Cat. No. 15596-026) was added. After the cells fully were lysed, 1/5 volume of chloroform was added. The mixture was mixed well, placed at room temperature for 20 min and then centrifuged at 4° C. at 12000 rpm for 20 min. The upper aqueous solution was taken, and an equal volume of isopropanol was added. The mixture was placed at room temperature for 20 min, and centrifuged at 4° C. at 12000 rpm for 20 min. The supernatant aqueous solution was discarded, and washed with 75% of ethanol twice. After centrifuging at 4° C. at 12000 rpm for 5 min, the aqueous solution was discarded and the precipitate was kept. After air drying at room temperature, DEPC water was added to re-suspend the precipitate to obtain RNA. The obtained RNA was transcribed reversely into cDNA using Roche reverse transcription kit Transcriptor First Strand cDNA Synthesis Kit (Roche Applied Science, Cat. No. 4897030001) according to the instructions thereof. The steps for constructing the phage library were carried out according to the method described in Carlos F. Barbas III, Phage display: A laboratory manual. The phage library IL4R Q14 was constructed with the mouse numbered IL4R Q14, with a library capacity of $9.28 \times 10^8$; the phage library IL4R Q6 was constructed with the mouse numbered IL4R Q6, with a library capacity of $2.8 \times 10^8$; and the phage library IL4R Q29 was constructed with the mouse numbered IL4R Q29, with a library capacity of $6.4 \times 10^8$.

1.3 Screening

1. Plate screening: The plate was coated with the IL4R-His protein (Sinobiological Co., Ltd., 10402-H08H) at 1 μg/well, left to stand overnight at 4° C., and blocked with 2% BSA for 1 h on the next day. The phage library ($2 \times 10^{12}$) was added and incubated for 2 h. After washing for 4-10 times, the IL4R-bound phage was eluted with an elution buffer (pH 2.2).

2. Magnetic bead screening: the IL4R-Fc protein (Sinobiological Co., Ltd., 10402-H02H) was biotinylated according to conventional steps (the molar ratio of the input IL4R protein to biotin was 1:2) before binding to magnetic beads (Thermo Co., Ltd.) (Invitrogen Dynabeads M-280 Streptavidin, 00355871), and then incubated with the phage library. After washing 4-10 times, the phage specifically bound to IL4R was eluted with an elution buffer (pH 2.2).

Clones IL4RQ14-BA030BA034, IL4RQ6-BA167BA173, IL4RQ24-BA420 and IL4RQ29-BA1301 were obtained by plate screening. IL4RQ14 represents the immunized 14th wild-type mouse, and BA represents magnetic bead screening.

The positive library detected by phage enzyme-linked immune assay (Elisa) was coated on a plate. The clones were picked out directly for induced expression by means of using an autonomous medium. The supernatant was detected for binding activity, and the selected clones were continued to be detected the blocking of IL4 expression by ELISA. The clones with IL4 blockade activity were selected for another ELISA detection, and positive clones that can block IL13/IL13RA1 were selected. Molecular construction and production of these positive clones were performed.

Example 2. Molecular Construction and Production of Blocking Antibodies

The clones IL4RQ14-BA030, BA034 (abbreviated as BA030 and BA034 in the present invention), IL4RQ6-BA167, BA173 (abbreviated as BA167 and BA173 in the present invention), IL4RQ24-BA420 (abbreviated as BA1301 in the present invention), and IL4RQ29-BA1301 (abbreviated as BA1301 in the present invention) were sent to Invitrogen Biotechnology Co., Ltd for sequencing. The amino acid sequence of each clone was shown in Table 1:

TABLE 1

Amino acid sequences of clones with blockade activity

| Clone ID | Light chain sequence | Heavy chain sequence |
|---|---|---|
| BA030 | DIVMTQSPSTLSASVGDRVTITCRASQS ISNWLAWYQQKPGKAPKRLIYKASSL ESGVPSRFSGSGSGTEFTLTISSLQPDDF ATYYCQQYNRYFTFGQGTKLEIK (SEQ ID NO: 17). | QVQLVESGGGVVQPGRSLRLSCAASGFTFS SYAIHWVRQAPGKGLEWVAVISYDGSKKY YADSVKGRFTISRDNSKNTLYLQMNSLRAE DTAVYYCAREYYYGMDVWGQGTTVTVSS (SEQ ID NO: 18). |
| BA034 | DIQMTQSPSTLSASVGDRVTITCRASQS FNSWLAWYQQKPGKAPKLLIYKSSRL ESGVPSRFSGSGSGTEFTLTISSLQPDDF ATYYCQQYNGYSWTFGQGTKVEIK (SEQ ID NO: 19) | QVQLVESRGGAVQPGRSLRVSCAASGFTFS SHGMDWVRQVPGKGLEWVAVISYDGKKK YYADSVKGRFTISRDNSKNTLYLQMNSLR AEDTAIYYCVKESRYYYGMDVWGQGTTV TVSS (SEQ ID NO: 20) |
| BA167 | EIVMTQSPSSLSASLGDRVTITCRASQN IGSRLAWYQQKPGKAPKLLIYKASSLE SGVPSRFSGSGSGTEFTLTISSLQPDDFA TYYCQQYNSYSWTFGQGTKLEIK (SEQ ID NO: 1) QNIGSR (SEQ ID NO: 3) KAS (SEQ ID NO: 4) QQYNSYSWT(SEQ ID NO: 5) | QVQLVESGGGVVQPGRSLRLSCAASGFTFS SYAMHWVRQAPGKGLEWVAVISYDGSNK YYADSVKGRFTISRDNSKNTLYLQMNSLR AEDTAVYYCARGLTTVRGVLYWGQGTLVT VSS (SEQ ID NO: 2) GFTFSSYA(SEQ ID NO: 6) ISYDGSNK(SEQ ID NO: 7) ARGLTTVRGVLY(SEQ ID NO: 8) |
| BA173 | DIVMTQSPSTLSASVGDRVTITCRASQS ISTRLAWYQQKPGKAPKLLVYWASSL ESGVPSRFSGSGSGTEFTLAISSLQPDD FGTYYCQQYTSYSWTFGQGTKLEIK (SEQ NO: 9) QSISTR (SEQ ID NO: 11) WAS (SEQ ID NO: 12) QQYTSYSWT (SEQ ID NO: 13) | QVQLVESGGGVVQPGRSLRLSCAASGFTFS SYAMHWVRQAPGKGLEWVAVISYDGSNK YYADSVKGRFTISRDNSKNTLYLQMNSLR AEDTAVYYCARGLTTVRGVLYWGQGTLVT VSS (SEQ NO: 10) GFTFSSYA (SEQ ID NO: 14) ISYDGSNK (SEQ ID NO: 15) ARGLTTVRGVLY (SEQ ID NO: 16) |
| BA420 | DIVMTQSPSTLSASVGDRVTITCRASPS ISSWLAWYQQKPGKAPKVLIYKSSRLE SGVPSRFSGNGSGTEFTLTISSLQPDDF ATYYCQQYNGYSWTFGQGTKVEIK (SEQ ID NO: 21) | QVQLVESGGGAVQPGRSLRVSCAASGFTFS SHGMDWVRQVPGKGLEWVAVISYDGKKK YYADSVKGRFTISRDNSKNTLYLQMNSLR AEDTAIYYCVKESRYYYGMDVWGQGTTV TVSS (SEQ ID NO: 22) |
| BA1301 | DIQMTQSPSTLSASVGDRVTITCRASQS ITRRLAWYQQKPGKAPKLLIYKASSLE SGVPSRFSGSGSGTEFTLTISSLQPDDFA TYYCQQYVSFSRTFGQGTKVEIK (SEQ ID NO: 23) | QVQLVESGGGVVQPGRSLRLSCAASGLTFS SYAMHWVRQAPGKGLEWVAVISYDGSNK YYADSVKGRFTISRDNSKNTLYLQMNSLR AEDTAVYYCARGFGYFDLWGRGTLVTVSS (SEQ ID NO: 24) |

Variable region gene amplification (2*EasyPfu PCR SuperMix, Manufacturer: Transgen, Cat. No.: AS211, Batch No.: #L11228) and signal peptide and variable region overlap extension were performed by conventional molecular biology technology. The variable region with heavy chain and signal peptide genes was linked to the vector pCDNA3.4 (Life Technology) with the sequence of the antibody heavy chain constant region (IgG4) by homologous recombination (ClonExpress II One Step Cloning Kit, Manufacturer: Vazyme, Cat. No.: C112-01, Batch No.: TE222B8); and the variable region with light chain and signal peptide genes was linked to the vector pCDNA3.4 (Life Technology) with the sequence of the antibody light chain constant region by homologous recombination (ClonExpress II One Step Cloning Kit, Manufacturer: Vazyme, Cat. No.: C112-01, Batch No.: TE222B8). The sequences were shown as follows.

Heavy chain constant region (IgG4) sequence:
(SEQ ID NO: 25)
ASTKGPSVFPLAPCSRSTSESTAALGCLVDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

-continued

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLG-

Light chain constant region sequence:
(SEQ ID NO: 26)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC-

Then the resulting vectors were co-transfected into HEK293 cells, which were cultured on a shaker at 37° C., 8% CO$_2$, 125 rpm. After 6-7 days, the transient expression supernatant was purified by Protein A affinity chromatography to obtain IL4R antibody, and the antibody concentration was determined by UV280 combined extinction coefficient.

Production of control antibody: The amino acid sequence of Dupilumab, an IL4R antibody of Regeneron Co., Ltd., was determined through IMGT data and patent US 2008160035 A1. After complete gene synthesis, the gene was inserted into vector pCDNA3.4 and expressed by HEK293 cells. The amino acid sequence of Dupilumab was shown as follows:

```
Light chain amino acid sequence of Dupilumab:
                                       (SEQ ID NO: 27)
DIVMTQSPLSLPVTPGEPASISCRSSQSLLYSIGYNYLDWYLQKSGQSPQ

LLIYLGSNRASGVPDRFSGSGSGTDFTLKISRVEAEDVGFYYCMQALQTP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Heavy chain amino acid sequence of Dupilumab:
                                       (SEQ ID NO: 28)
EVQLVESGGGLEQPGGSLRLSCAGSGFTFRDYAMTWVRQAPGKGLEWVSS

ISGSGGNTYYADSVKGRFTISRDNSKNTLYLQMNSLRAEDTAVYYCAKDR

LSITIRPRYYGLDVWGQGTTVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

G-
```

Figure 2:
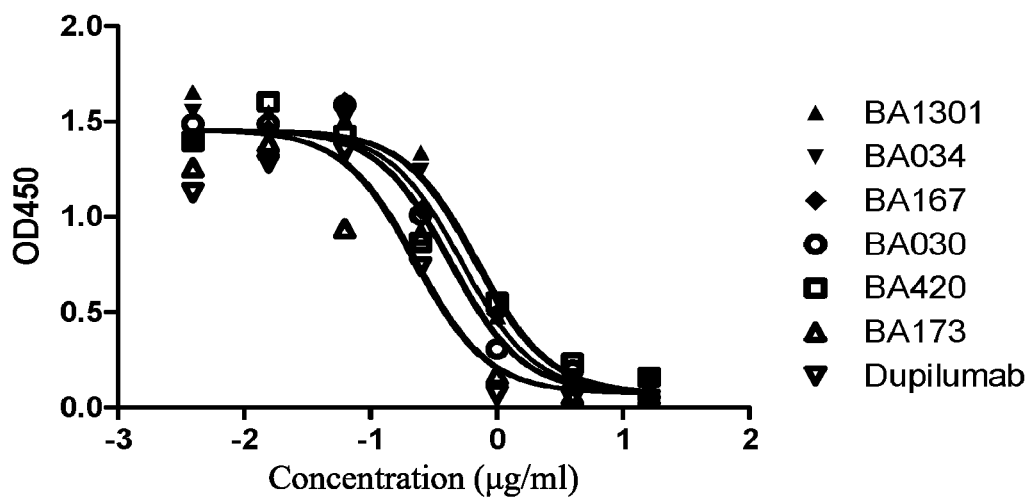
FIG. 2 shows comparison of candidate antibodies in blocking protein-binding activity of IL4/IL4R.

Example 3 Comparison of BA030, BA167, BA173 and Dupilumab 3.1 Comparison of Blockade Activities of Screening Antibody and IL4R Protein IL4 (11846-HANE, Sinobiological Co., Ltd.) was coated at the concentration of 0.2 μg/ml in 100 μL/well at 4° C. overnight; 3% skimmed milk powder was used for blocking 1 h; at the same time, 50 μL of IL4R-Fc-biotin (0.4 μg/ml) and 50 μL of candidate antibody at different concentrations (16 μg/mL, 4 μg/mL, 1 μg/mL, 0.25 μg/mL, 0.0625 μg/mL, 0.015625 μg/mL, and 0.00390625 μg/mL), 100 μL in total, were added to the blocked ELISA plate and co-incubated at 37° C. for 1 h; after washing three times with PBST, streptomycin/HRP (R&D, Cat. No.: 890803) was added, and incubated at 37° C. for 1 h; and 100 μL of TMB color developing solution (Beijing Meike Wande Co., Ltd., Cat. No.: 1001) was added to each well. Color development was stopped, after 10 min color development, with the addition of 50 L of 2 M concentrated sulfuric acid, and OD450 was measured with a microplate reader. The results were shown in FIG. 2 and Table 2.

After comprehensively analyzing antibody sequences, blocking data, etc., we choosed IL4R-BA167-IgG4 (hereinafter or abbreviated as BA167), IL4R-BA173-IgG4 (hereinafter or abbreviated as BA173), IL4R-BA030-IgG4 (hereinafter or abbreviated as BA030) and Dupilumab antibody for comparison experiments.

Figure 3:
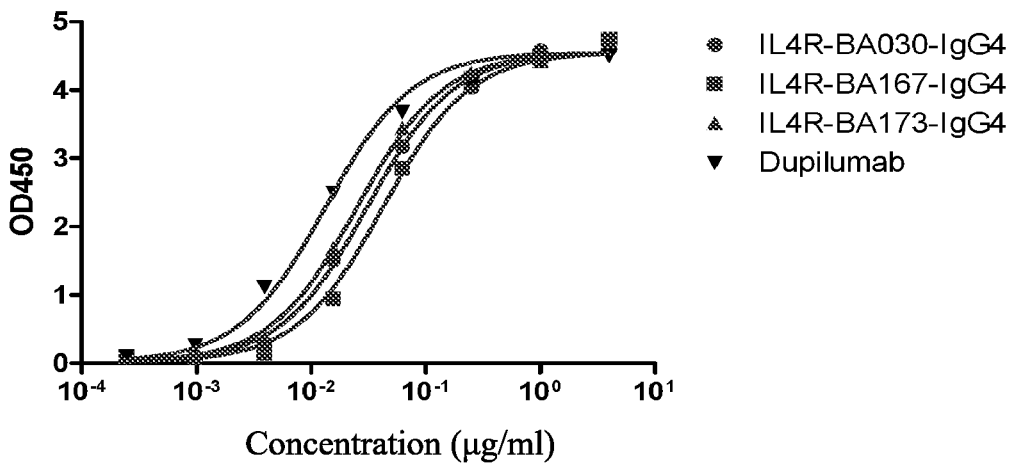
FIG. 3 shows comparison of binding activities of BA167, BA173, BA030, Dupilumab and IL4R protein.

3.2 Comparison of Binding Activities of BA167, BA173, BA030, and Dupilumab with IL4R Protein CBS coating solution (pH 9.6 carbonic acid solution) was used to coat protein IL4R (10402-H08H, Sinobiological Co., Ltd.) at different concentrations (0.4 μg/ml, 0.2 μg/ml, 0.1 μg/ml, 0.05 μg/ml, 0.025 μg/ml, 0.0125 ag/ml, 0.00625 ag/ml and 0 g/ml) in 100 μL/well at 4° C. overnight; 3% skimmed milk powder was used for blocking 1 h at 37° C.; 100 μL of candidate antibody at 2 μg/ml was added to each well and incubated at 37° C. for 1 h; and then goat anti-human IgG (H+L)/HRP (KPL, Cat. No.: 474-1006) was added, and incubated at 37° C. for 1 h. Color development was stopped, after 10 min color development, with the addition of 50 μL of 2 M H$_2$SO$_4$ to each well, and OD450 was measured with a microplate reader. The results were shown in FIG. 3 and Table 3. Compared with the control antibody, 3 antibodies had close binding sensitivity to IL4R protein.

TABLE 3

| Sample | Binding sensitivity to IL4R protein | | | |
| --- | --- | --- | --- | --- |
| | IL4R-BA030-IgG4 | IL4R-BA167-IgG4 | IL4R-BA173-IgG4 | Dupilumab |
| EC50 (μg/mL) | 0.031 | 0.045 | 0.025 | 0.012 |

3.3 Candidate Antibodies in Blocking Protein-Binding of IL4/IL4R

Figure 4:
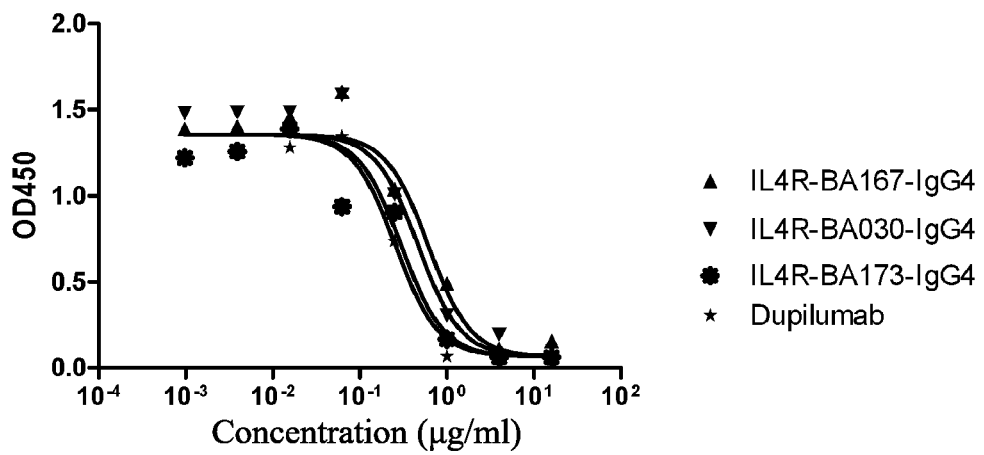
FIG. 4 shows comparison of BA167, BA173, BA030, and Dupilumab in blocking the protein binding activity of IL4/IL4R.

IL4 (11846-HANE, Sinobiological Co., Ltd.) was coated at the concentration of 0.2 μg/ml in 100 μL/well at 4° C. overnight; 3% skimmed milk powder was used for blocking 1 h; at the same time, IL4R-Fc-biotin (0.4 μg/ml) and candidate antibody at different concentrations (30 μg/mL, 7.5 μg/mL, 1.875 μg/mL, 0.46875 μg/mL, 0.1171875 μg/mL and 0 μg/mL) were co-incubated at 37° C. for 1 h, then added to the blocked ELISA plate and co-incubated at 37° C. for another 1 h; then streptomycin/HRP (R&D, Cat. No.: 890803) was added, and incubated at 37° C. for 1 h; color development was stopped, after 10 min color development, with the addition of 50 μL of 2M H$_2$SO$_4$ to each well. OD450 was measured with a microplate reader. The results were shown in FIG. 4 and Table 4. Compared with the control antibody, 3 antibodies can effectively block the binding of IL4 and IL4R, and had a similar blockade activity.

TABLE 2

| Candidate antibodies in blocking protein-binding activity of IL4/1L4R | | | | | | | |
| --- | --- | --- | --- | --- | --- | --- | --- |
| Sample | Dupilumab | BA420 | BA030 | BA173 | BA167 | BA1301 | BA034 |
| IC50 (μg/ml) | ~0.257 | 0.334 | 0.343 | 0.354 | 0.458 | 0.592 | 0.71 |

TABLE 4

| | Protein name | | | |
|---|---|---|---|---|
| | IL4R-BA167-IgG4 | IL4R-BA030-IgG4 | IL4R-BA173-IgG4 | Dupilumab |
| IC50 µg/ml | 0.477 | 0.346 | 0.367 | ~0.2602 |

3.4 Candidate Antibodies in Blocking Protein-Binding of IL13+IL13RA1/IL4R

Figure 5:
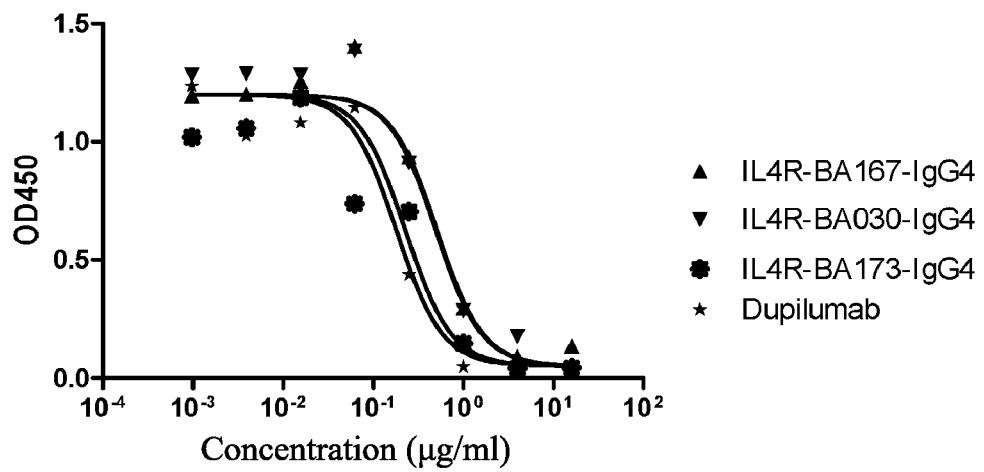
FIG. 5 shows comparison of BA167, BA173, BA030, and Dupilumab in blocking the protein binding activity of IL13+ IL13RA1/IL4R.

IL13RA1 (10943-H08H, Sinobiological Co., Ltd.) was coated at the concentration of 0.8 µg/ml in 100 µL/well at 4° C. overnight; 3% skimmed milk powder was used for blocking 1 h; at the same time, IL4R-Fc-biotin (0.24 µg/ml) and IL13 (1 µg/ml, 10369-HANE, Sinobiological Co., Ltd.) and candidate antibody at different concentrations (30 µg/mL, 7.5 µg/mL, 1.875 µg/mL, 0.46875 µg/mL, 0.1171875 µg/mL and 0 µg/mL) were co-incubated at 37° C. for 1 h, then added to the blocked ELISA plate and co-incubated at 37° C. for another 1 h; after washing three times with PBST, streptomycin/HRP (R&D, Cat. No.: 890803) was added, and incubated at 37° C. for 1 h; and after washing four times with PBST, TMB was used for color development for 10 min. 50 µL of 2M $H_2SO_4$ was added to each well to stop color development. OD450 was measured with a microplate reader. The results were shown in FIG. 5 and Table 5. Compared with the control antibody, 3 antibodies can effectively block the binding of IL13+IL13RA1 and IL4R, and had a similar blockade activity.

TABLE 5

Blocking the protein binding activity of IL13 + IL13RA1/IL4R

| | Protein name | | | |
|---|---|---|---|---|
| | IL4R-BA167-IgG4 | IL4R-BA030-IgG4 | IL4R-BA173-IgG4 | Dupilumab |
| IC50 µg/ml | 0.4071 | 0.3809 | 0.3025 | ~0.2396 |

3.5 Binding of BA167, BA173, BA030 and Dupilumab in Different Species

The Elisa method was used to detect the binding of BA167, BA173, BA030 and Dupilumab to human, mouse and cynomolgus IL4R, respectively.

CBS coating solution (pH 9.6 carbonic acid solution) was used to coat human IL4R (10402-H08H, Sinobiological Co., Ltd.), Rhesus IL4R (ILR-C52H8, ACRO) and Mouse IL4R (ILR-M52H1, ACRO) at different concentrations (5 µg/ml, 1.25 g/ml, 0.3125 µg/ml and 0.078125 µg/ml) in 100 µL/well at 4° C. overnight; 3% skimmed milk powder was used for blocking 1 h at 37° C.; 100 µL of candidate antibody at 5 µg/ml was added to each well and incubated at 37° C. for 1 h; and then goat anti-human IgG/HRP (KPL, Cat. No.: 474-1006) was added, and incubated at 37° C. for 1 h. After washing four times with PBST, TMB was used for color development for 10 min. 50 µL of 2M $H_2SO_4$ was added to each well to stop color development. OD450 was measured with a microplate reader.

Figure 6:
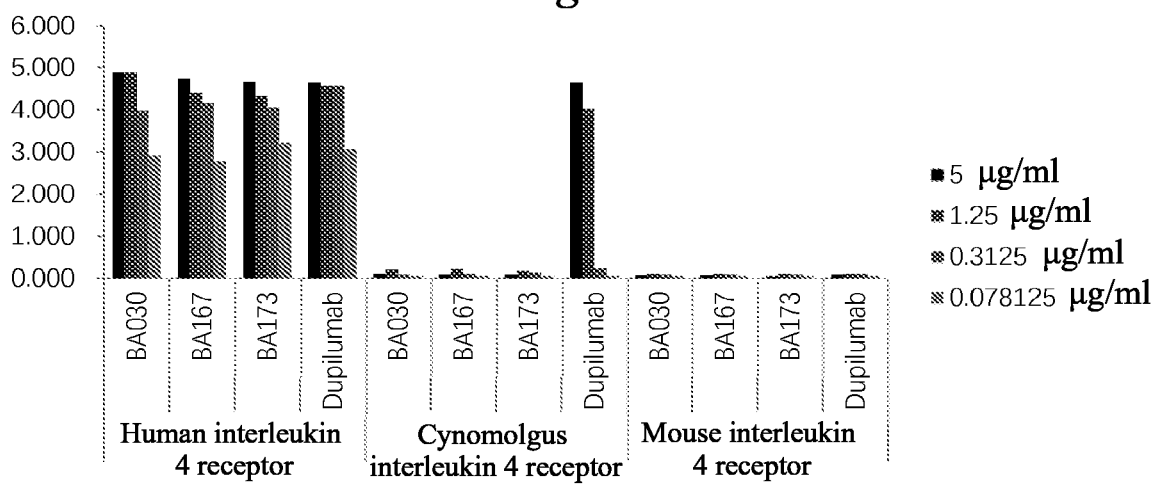
FIG. 6 shows the binding differences of BA167, BA173, BA030 and Dupilimab with Human/Rhesus/Mouse IL4R.

The results showed that the four groups of antibodies had similar binding to human IL-4R protein, but had different binding performances on cynomolgus IL4R protein, as shown in FIG. 6. The results indicated that BA167, BA173 and BA030 antibodies and Dupilumab had different epitopes on IL4R.

3.6 Comparison of BA030, BA167, BA173 and Dupilumab Antibody in Cell function in vitro 3.6.1 Experiment on Inhibiting TF-1 Cell Proliferation Induced by IL4

Figure 7:
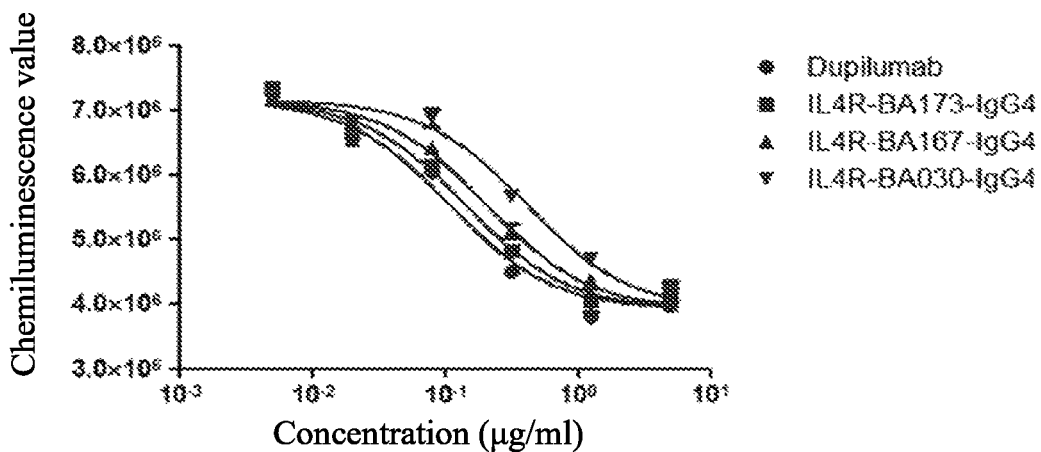
FIG. 7 shows the experiment on inhibiting TF-1 cell proliferation induced by IL4.

TF-1 cells, IL4 (Sinobiological, Cat. No.: 11846-HNAE) and antibodies were all diluted with complete medium (90% RPMI 1640, 10% FBS). TF-1 cells were diluted to $4\times10^5$ cells/mL, and inoculated in a white 96-well plate at 50 µL/well, i.e., 20000 cells/well. IL4 was diluted to 2 ng/mL. The antibodies were diluted to 5 µg/mL, and then diluted 4 times in sequence (6 concentrations in total). The diluted antibodies and IL4 were mixed in equal volumes and then the mixture was added to cell wells in 50 µL/well. 1 ng/mL of IL4 was added to the cell well as a negative control. Complete medium was added to the cell wells as a positive control. Replicate wells were set for all samples. After culturing for 96 h, the cell mass was detected using a CellTiter-Glo (Promega, Cat. No.: G7572) kit. The experimental results are shown in FIG. 7 and Table 6.

3.6.2 Experiment on Inhibiting TF-1 Cell Proliferation Induced by IL13

Figure 8:
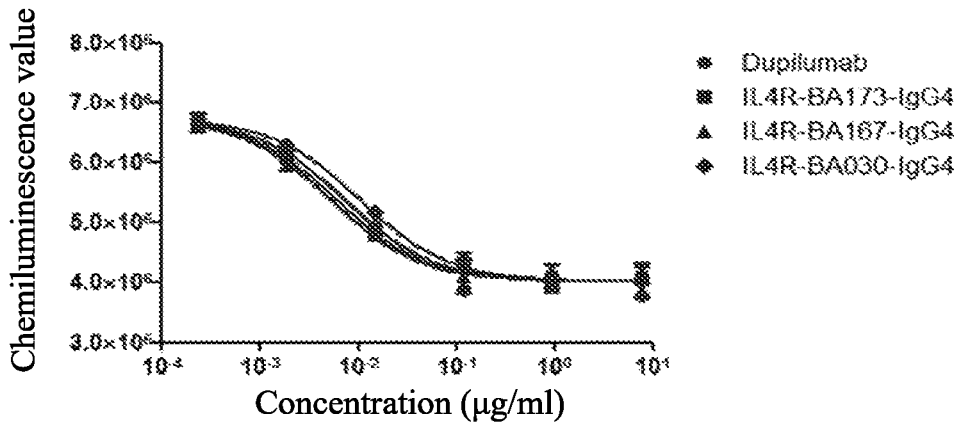
FIG. 8 shows the experiment on inhibiting TF-1 cell proliferation induced by IL13.

TF cells, IL13 (Sinobiological, Cat. No.: 10369-HNAC) and antibodies were all diluted with complete medium (90% RPMI 1640, 10% FBS). TF-1 cells were diluted to $4\times10^5$ cells/mL, and inoculated in a white 96-well plate at 50 µL/well, i.e., 20000 cells/well. IL13 was diluted to 4 ng/mL. The antibodies were diluted to 7.5 µg/mL, and then diluted 8 times in sequence (6 concentrations in total). The diluted antibodies and IL13 were mixed in equal volumes and then the mixture was added to cell wells in 50 µL/well. 2 ng/mL of IL13 was added to the cell well as a negative control. Complete medium was added to the cell wells as a positive control. Replicate wells were set for all samples. After culturing for 96 h, the cell mass was detected using a CellTiter-Glo (Promega, Cat. No.: G7572) kit. The experimental results were shown in FIG. 8 and Table 6.

3.6.3 Inhibitory Effects on the Proliferation of PBMC Cells

Figure 9:
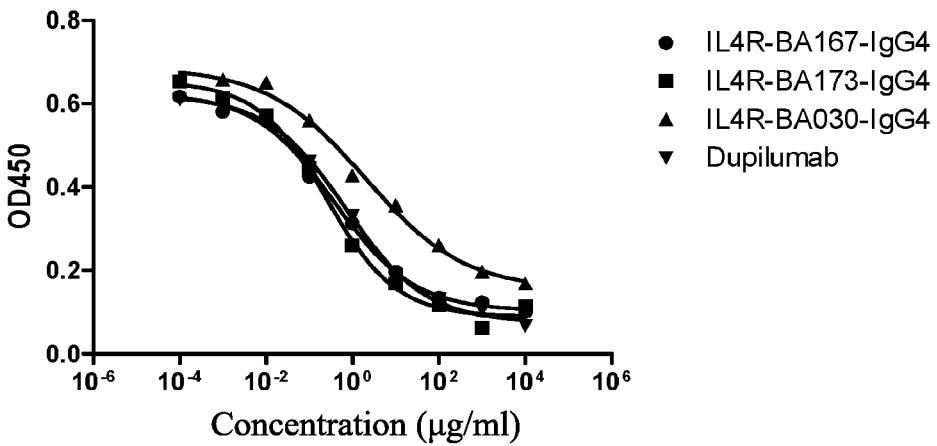
FIG. 9 shows the inhibitory effects of candidate antibodies on the proliferation of PBMC cells.

IL4 can promote the proliferation of PBMC cells. After the antibodies were added, the antibodies were bound to the receptor of IL4 and inhibited the proliferation of PBMC cells. Cells, IL4 (Sinobiological, Cat. No.: 11846-HNAE) and antibodies were all diluted with complete medium (90% RPMI 1640, 10% FBS). PBMC was recovered, and PHA (Thermo, Cat. No.: 10576015) was added at a ratio of 1:100 for culturing 4 days. The antibodies were diluted to 160 µg/mL, and diluted 10 times in sequence (9 concentrations in total). IL4 was diluted to 400 ng/mL. The antibodies and IL4 were mixed in equal volumes and the mixture was added to a 96-well plate in 50 µL/well. PHA-treated PBMC was added in 50 µL/well. 10 µL of CCK8 (Dojindo, Cat. No.: CK08) was added to each well. After color development for 4 h, OD450 nm was measured. The experimental results were shown in FIG. 9 and Table 6.

TABLE 6

Data statistics of cell activity IC50

| | Antibody ID | | |
|---|---|---|---|
| | TF-1 Cells | | PBMC |
| | IC50 (IL4, ng/mL) | IC50 (IL13, ng/mL) | IC50 (IL4, ng/mL) |
| Dupilumab | 65 | 9 | 2.868 |
| IL4R-BA173-IgG4 | 66 | 6 | 1.018 |
| IL4R-BA167-IgG4 | 139 | 5 | 1.525 |
| IL4R-BA030-IgG4 | 227 | 9 | 8.086 |

TF-1 is a human hematological leukemia cell. IL4 and IL13 can induce the growth of TF-1 cells by binding to cell surface receptors. After the antibodies were added, the antibodies bound to the receptors of IL4/IL13, thereby inhibiting the growth of TF-1 cells. From the above-mentioned 3.6.1-3.6.2 experiments, it can be found that in the experiment on inhibiting cell proliferation of TF-1, the inhibitory effect of BA173 antibody on IL-4 induced TF-1 cell proliferation was better than other candidate antibodies, and BA173 had a similar blockade activity to Dupilumab. In the 3.6.3 experiment, BA173 and BA167 had better effects of action than Dupilumab, indicating that the two antibodies can better bind to the IL4 receptor, thereby inhibiting the proliferation of PBMC.

Figure 10:
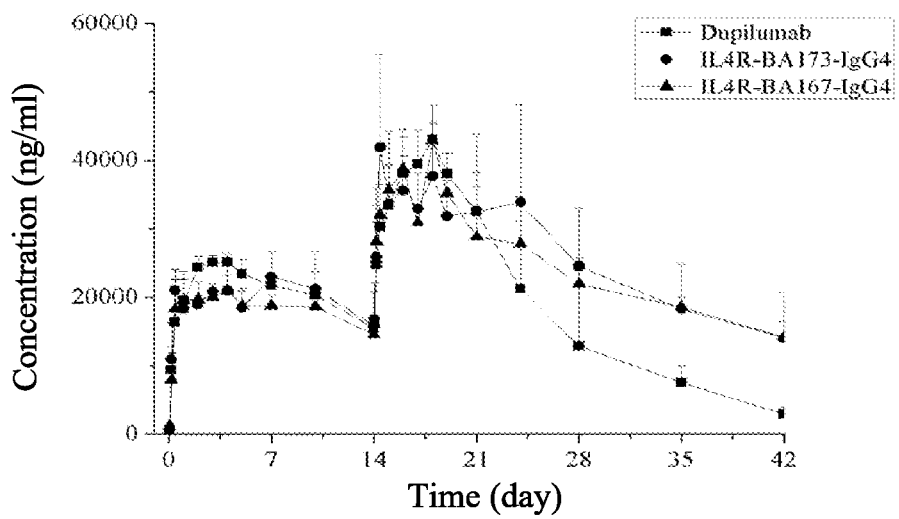
FIG. 10 shows the in vivo average concentration-time curve of cynomolgus after subcutaneous injection of 2.5 mg/kg prescribed BA167, BA173, and Dupilumab.

Example 4 Study of BA167, BA173 and Dupilumab on PK of Cynomolgus 3 cynomolgus for each antibody were selected for subcutaneous injection administration at a dose of 2.5 mg/kg, and administrated twice. The second administration time was 14 days (d means day), 0 h before administration and 1 h, 4 h, 10 h, 1 d, 2 d, 3 d, 4 d, 5 d, 7 d, 10 d, 14 d after administration. 1 h, 4 h, 10 h, 1 d, 2 d, 3 d, 4 d, 5 d, 7 d 10 d, 14 d, 21 d and 28 d after the second administration, serums were collected to detect the antibody concentrations. The method for detecting the serum was Elisa method. The specific detection results are shown in FIG. 10 and Table 7 below.

TABLE 7

Pharmacokinetic parameters of cynomolgus after subcutaneous injection of 2.5 mg/kg prescribed BA167, BA173, and Dupilumab

| Antibody ID | $T_{1/2}$ day | Tmax day | $C_{max}$ ng/mL | $AUC_{last}$ d * ng/mL | Vz mL/kg | CL mL/d/kg | $AUC_{1st}$ d * ng/mL | $AUC_{2st}$ d * ng/mL | $AUC_{2st}$ Fold |
|---|---|---|---|---|---|---|---|---|---|
| Dupilumab | 4.2 | 18 | 44636.6 | 781485.7 | 17.5 | 3.2 | 290271.9 | 491263.6 | |
| IL4R-BA173-IgG4 | 15.7 | 15.6 | 42284.2 | 994342.3 | 45.2 | 2 | 277345.5 | 716996.8 | 1.5x |
| IL4R-BA167-IgG4 | 22.2 | 18 | 42914.3 | 937874.6 | 56.8 | 1.8 | 254696.9 | 683177.7 | 1.4x |

After the second subcutaneous administration of Dupilumab, BA173, and BA167 to cynomolgus, different accumulation degrees appeared, with Cmax2/Cmax1 values closing to 2, and AUC2st/AUC1st values ≥2. The T½ values calculated based on the elimination phase of the second dosing end were 4.2 3.0 d, 15.7±1.9 d, and 22.2±8.1 d, respectively. From the above-mentioned data, it can be found that BA167 and BA173 lasted longer in the serum of cynomolgus after administration. Compared with the weekly administration of Dupilumab, the administration period can be significantly prolonged.

Figure 11:
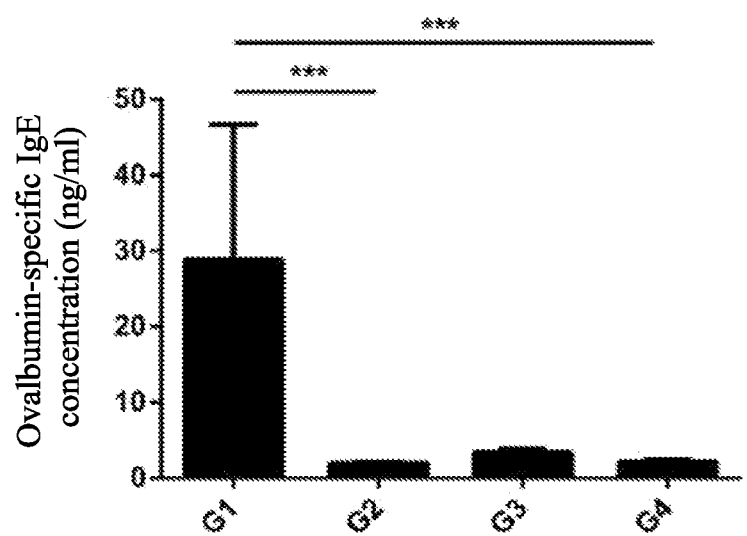
FIG. 11 shows the changes of IgE levels in serum of B-hIL4/hIL4Rα double humanized asthma model mice after administration.
Figure 12:
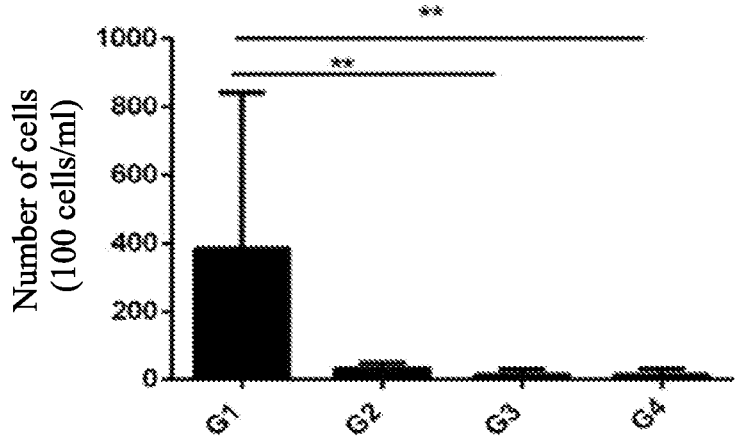
FIG. 12 shows the changes of BALF eosinophils in serum of B-hIL4/hIL4Rα double humanized asthma model mice after administration.

Example 5 Drug Efficacy Experiment of BA167, BA173 and Dupilumab Based on B-hIL-4/hIL-4RA Double Humanized Mouse Asthma Model 40 μg OVA (ovalbumin) was formulated, and the mice were sensitized with intraperitoneal injection (200 μL/mouse). The sensitization time was on day 0, 7, and 14. During day 21-25, 2% OVA was inhaled by atomizing for challenge (30 min each time for 5 consecutive days). The test mice were administered on the day 20 and 23, and 24 hours after the last challenge operation, samples were collected for analysis. 24 hours after the last atomization and challenge operation, the peripheral blood of the mice was collected, and the serum was detected for OVA-specific IgE antibody. Alveolar lavage fluid was collected for OVA-specific IgE antibody detection. 24 hours after the last atomization and challenge operation, the mouse alveolar lavage fluid was collected for detecting eosinophil infiltration by flow cytometry. The experimental results are shown in FIG. 11 and FIG. 12 (G1: 1× Buffer; G2: Dupilumab; G3: BA173; G4: BA167).

At the end of the experiment, the average IgE level in serum of the G1 control group was 28.85 ng/mL, and the IgE levels in the Dupilumab, BA173 and BA167 groups were 2.0 ng/mL, 3.4 ng/mL, and 2.1 ng/mL, respectively; The average number of eosinophils in the control group was $384.50 \times 10^2$ (cells/mL), and the number of eosinophils in the Dupilumab, BA173 and BA167 groups were $31.1 \times 10^2$ (cells/mL), $12.8 \times 10^2$ (cells/mL) and $14.0 \times 10^2$ (cells/mL), respectively. In the drug efficacy model of the experiment, the BA167 and BA173 groups can significantly reduce the IgE level in the serum of asthma model mice and the number of eosinophils in the alveolar lavage fluid at a dose of 25 mg/kg. The BA167 and BA173 groups effectively alleviated asthma and contributed to reduce the incidence of asthma exacerbations, improved asthma-related evaluation parameters, and improved the dependence of a patient on an inhaled corticosteroid and/or a long-acting β agonist.

At the same time, in the animal models of atopic dermatitis, pruritus, neutropenia, allergic reaction, nasal polyp, eosinophilic esophagitis, skin infection, and chronic sinusitis, each group of animals were administered, respectively. The result showed that candidate antibodies BA173 and BA167 both show similar effects in the above-mentioned animal models to those in asthma models, exhibiting good alleviation or treatment effects on atopic dermatitis, pruritus, neutropenia, allergic reaction, nasal polyp, eosinophilic esophagitis skin infection and chronic sinusitis.

Example 6 Immunogenicity of BA167, BA173 and Dupilumab in Cynomolgus

CBS coating solution (pH 9.6 carbonic acid solution) was used to coat BA167, BA173 and Dupilumab at 0.125 μg/ml in 100 μL/well at 4° C. overnight; 3% skimmed milk powder was used for blocking 1 h at 37° C.; and 100 μL of 100× serum diluted with PBST was added to each well and incubated at 37° C. for 1 h; After washing twice with PBST, BA167-biotin, BA173-biotin and Dupilumab-biotin were added at 0.125 μg/ml (100 μL per well), and incubated at 37° C. for 1 h. After washing twice with PBST, streptomycin/HRP was added, and incubated at 37° C. for 1 h; and after washing four times with PBST, TMB was used for color development for 10 min. 50 μL of 2M $H_2SO_4$ was added to each well to stop color development. OD450 was measured with a microplate reader.

Figure 13A:
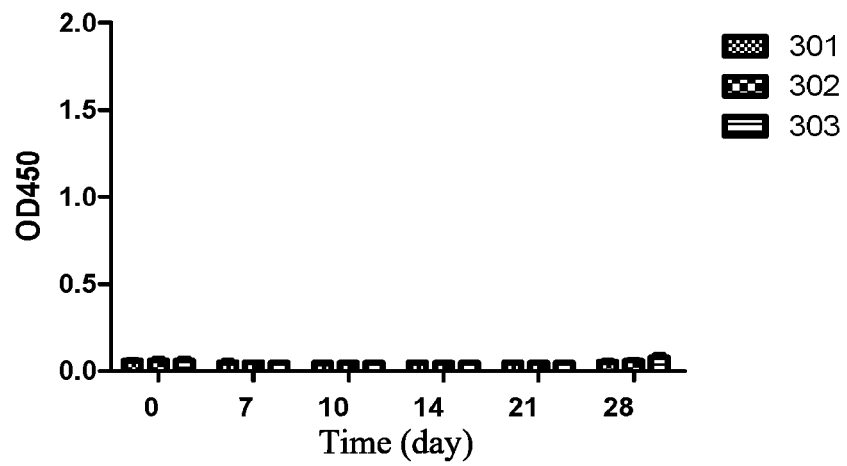
FIG. 13A-13C sequentially show the immunogenicity detection of BA173, BA167 and Dupilumab antibodies, respectively.
Figure 13B:
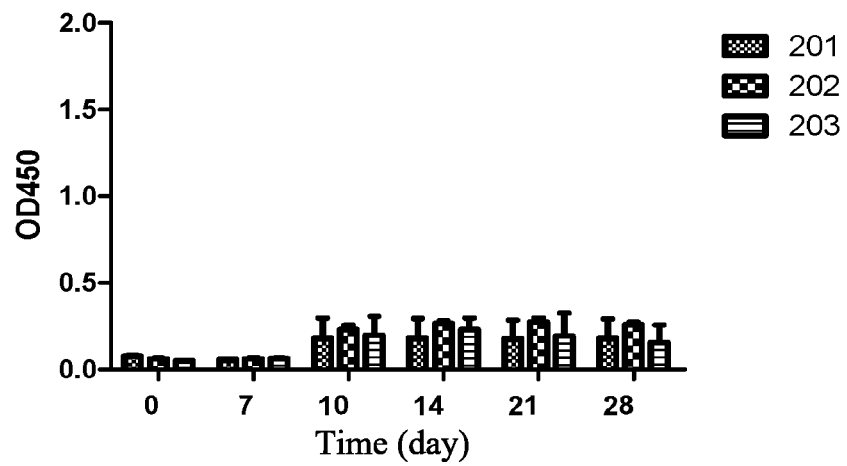
Figure 13C:
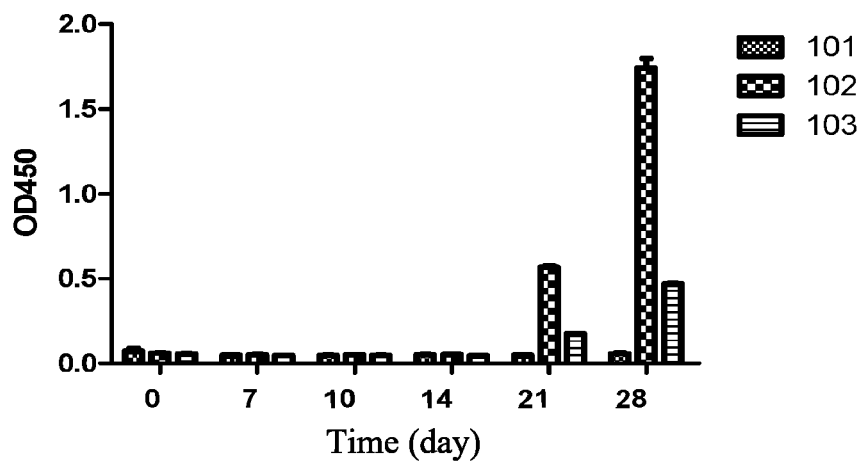

The results were shown in FIG. 13 (101-303 represented the number of cynomolgus). One cynomolgus in the Dupilumab experimental group developed strong immunogenicity on day 21, and the OD value was close to 2 on day 28. The OD values of BA173 and BA167 did not exceed 0.3, and there was no immunogenicity in cynomolgus. This indicated that our antibodies would have higher efficacy and higher safety in the future, have fewer side effects in the body after administration, and have lower liver toxicity.

The invention claimed is:

1. An antibody or antigen-binding fragment thereof wherein the antibody or antigen-binding fragment thereof binds to IL-4R antigen, wherein the antibody or antigen-binding fragment thereof comprises
   1) 3 light chain complementarity determining regions (LCDR1, LCDR2 and LCDR3, wherein LCDR1 amino acid sequence is as shown in SEQ ID NO: 11, LCDR2 amino acid sequence is as shown in SEQ ID NO: 12, and LCDR3 amino acid sequence is as shown in SEQ ID NO: 13, and
   3 heavy chain complementarity determining regions (HCDR1, HCDR2 and HCDR3), wherein HCDR1 amino acid sequence is as shown in SEQ ID NO: 14, HCDR2 amino acid sequence is as shown in SEQ ID NO: 15, and HCDR3 amino acid sequence is as shown in SEQ ID NO: 16; or
   2) 3 light chain complementarity determining regions (LCDR1, LCDR2 and LCDR3, wherein LCDR1 amino acid sequence is as shown in SEQ ID NO: 3, LCDR2 amino acid sequence is as shown in SEQ ID NO: 4, and LCDR3 amino acid sequence is as shown in SEQ ID NO: 5, and
   3 heavy chain complementarity determining regions (HCDR1, HCDR2 and HCDR3), wherein HCDR1 amino acid sequence is as shown in SEQ ID NO: 6, HCDR2 amino acid sequence is as shown in SEQ ID NO: 7, and HCDR3 amino acid sequence is as shown in SEQ ID NO: 8.

2. The antibody or antigen-binding fragment thereof of claim 1, wherein the antibody or antigen-binding fragment thereof comprises a light chain variable region with an amino acid sequence of SEQ ID NO: 1 and a heavy chain variable region with an amino acid sequence of SEQ ID NO: 2.

3. A pharmaceutical composition, wherein the pharmaceutical composition comprises the antibody or antigen-binding fragment thereof of claim 1 and a pharmaceutically acceptable carrier.

4. The antibody or antigen-binding fragment thereof of claim 1, wherein the antibody or antigen-binding fragment thereof comprises:
   3 light chain complementarity determining regions (LCDR1, LCDR2 and LCDR3), wherein LCDR1 amino acid sequence is as shown in SEQ ID NO: 11, LCDR2 amino acid sequence is as shown in SEQ ID NO: 12, and LCDR3 amino acid sequence is as shown in SEQ ID NO: 13, and
   3 heavy chain complementarity determining regions (HCDR1, HCDR2 and HCDR3), wherein HCDR1 amino acid sequence is as shown in SEQ ID NO: 14, HCDR2 amino acid sequence is as shown in SEQ ID NO: 15, and HCDR3 amino acid sequence is as shown in SEQ ID NO: 16.

5. The antibody or antigen-binding fragment thereof of claim 1, wherein the antibody or antigen-binding fragment thereof comprises:
   3 light chain complementarity determining regions (LCDR1, LCDR2 and LCDR3), wherein LCDR1 amino acid sequence is as shown in SEQ ID NO: 3, LCDR2 amino acid sequence is as shown in SEQ ID NO: 4, and LCDR3 amino acid sequence is as shown in SEQ ID NO: 5, and
   3 heavy chain complementarity determining regions (HCDR1, HCDR2 and HCDR3), wherein HCDR1 amino acid sequence is as shown in SEQ ID NO: 6, HCDR2 amino acid sequence is as shown in SEQ ID NO: 7, and HCDR3 amino acid sequence is as shown in SEQ ID NO: 8.

6. The antibody or antigen-binding fragment thereof of claim 1, wherein the antibody or antigen-binding fragment thereof comprises:
   a light chain variable region with an amino acid sequence of SEQ ID NO: 9, and a heavy chain variable region with an amino acid sequence of SEQ ID NO: 10.

7. An antibody or antigen-binding fragment thereof comprising
   1) a light chain variable region comprising LCDR1, LCDR2, and LCDR3 that are identical to LCDR1, LCDR2, and LCDR3 of SEQ ID NO: 1; and
   a heavy chain variable region comprising HCDR1, HCDR2, and HCDR3 that are identical to HCDR1, HCDR2, and HCDR3 of SEQ ID NO: 2; or
   2) a light chain variable region comprising LCDR1, LCDR2, and LCDR3 that are identical to LCDR1, LCDR2, and LCDR3 of SEQ ID NO: 9; and
   a heavy chain variable region comprising HCDR1, HCDR2, and HCDR3 that are identical to HCDR1, HCDR2, and HCDR3 of SEQ ID NO: 10 wherein the antibody or antigen binding fragment thereof binds to IL-4R antigen.

8. The antibody or antigen-binding fragment thereof of claim 7, comprising
   a light chain variable region comprising LCDR1, LCDR2, and LCDR3 that are identical to LCDR1, LCDR2, and LCDR3 of SEQ ID NO: 1; and
   a heavy chain variable region comprising HCDR1, HCDR2, and HCDR3 that are identical to HCDR1, HCDR2, and HCDR3 of SEQ ID NO: 2.

9. The antibody or antigen-binding fragment thereof of claim 7, comprising
  a light chain variable region comprising LCDR1, LCDR2, and LCDR3 that are identical to LCDR1, LCDR2, and LCDR3 of SEQ ID NO: 9; and
  a heavy chain variable region comprising HCDR1, HCDR2, and HCDR3 that are identical to HCDR1, HCDR2, and HCDR3 of SEQ ID NO: 10.

* * * * *

UNITED STATES PATENT AND TRADEMARK OFFICE
CERTIFICATE OF CORRECTION

PATENT NO. : 12,338,288 B2
APPLICATION NO. : 17/601837
DATED : June 24, 2025
INVENTOR(S) : Deyong Song, Chuangchuang Dong and Jing Han Page 1 of 1

It is certified that error appears in the above-identified patent and that said Letters Patent is hereby corrected as shown below:

In the Claims

In Column 37, Line 19 (Approx.), In Claim 1, after thereof insert -- , --.

In Column 37, Line 24 (Approx.), In Claim 1, delete "LCDR3," and insert -- LCDR3), --.

In Column 37, Line 36, In Claim 1, delete "LCDR3," and insert -- LCDR3), --.

In Column 38, Line 57, In Claim 7, after 10 insert -- , --.

In Column 38, Line 58, In Claim 7, delete "antigen binding" and insert -- antigen-binding --.

Signed and Sealed this
Nineteenth Day of August, 2025

Coke Morgan Stewart
*Acting Director of the United States Patent and Trademark Office*